(12) United States Patent
Anissian

(10) Patent No.: US 9,872,689 B1
(45) Date of Patent: Jan. 23, 2018

(54) KNEE ARTHROPLASTY PREPARATION DEVICES AND METHODS

(71) Applicant: Lucas Anissian, Shreveport, LA (US)

(72) Inventor: Lucas Anissian, Shreveport, LA (US)

(*) Notice: Subject to any disclaimer, the term of this patent is extended or adjusted under 35 U.S.C. 154(b) by 725 days.

(21) Appl. No.: 14/330,795

(22) Filed: Jul. 14, 2014

Related U.S. Application Data

(60) Provisional application No. 61/930,015, filed on Jan. 22, 2014.

(51) Int. Cl.
*A61B 17/58* (2006.01)
*A61B 17/60* (2006.01)
*A61F 2/00* (2006.01)
*A61B 17/17* (2006.01)

(52) U.S. Cl.
CPC .............. *A61B 17/1764* (2013.01)

(58) Field of Classification Search
CPC ... A61B 17/154; A61B 17/155; A61B 17/157; A61B 17/158; A61B 17/1764; A61B 17/025

USPC ................................................. 606/86 R, 88
See application file for complete search history.

(56) References Cited

U.S. PATENT DOCUMENTS

| 4,952,213 A * | 8/1990 | Bowman | A61B 17/157 |
| | | | 606/62 |
| 2011/0092977 A1 * | 4/2011 | Salehi | A61B 17/155 |
| | | | 606/88 |
| 2013/0310838 A1 * | 11/2013 | Kurtz | A61B 17/151 |
| | | | 606/88 |

* cited by examiner

*Primary Examiner* — Si Ming Ku
(74) *Attorney, Agent, or Firm* — R. Keith Harrison

(57) ABSTRACT

Knee arthroplasty preparation devices include a tibial cutting block adapted for attachment to a tibia, a femoral cutting block adapted for attachment to a femur and a block positioning guide engaging the tibial cutting block and the femoral cutting block. Knee arthroplasty preparation methods are also disclosed.

17 Claims, 8 Drawing Sheets

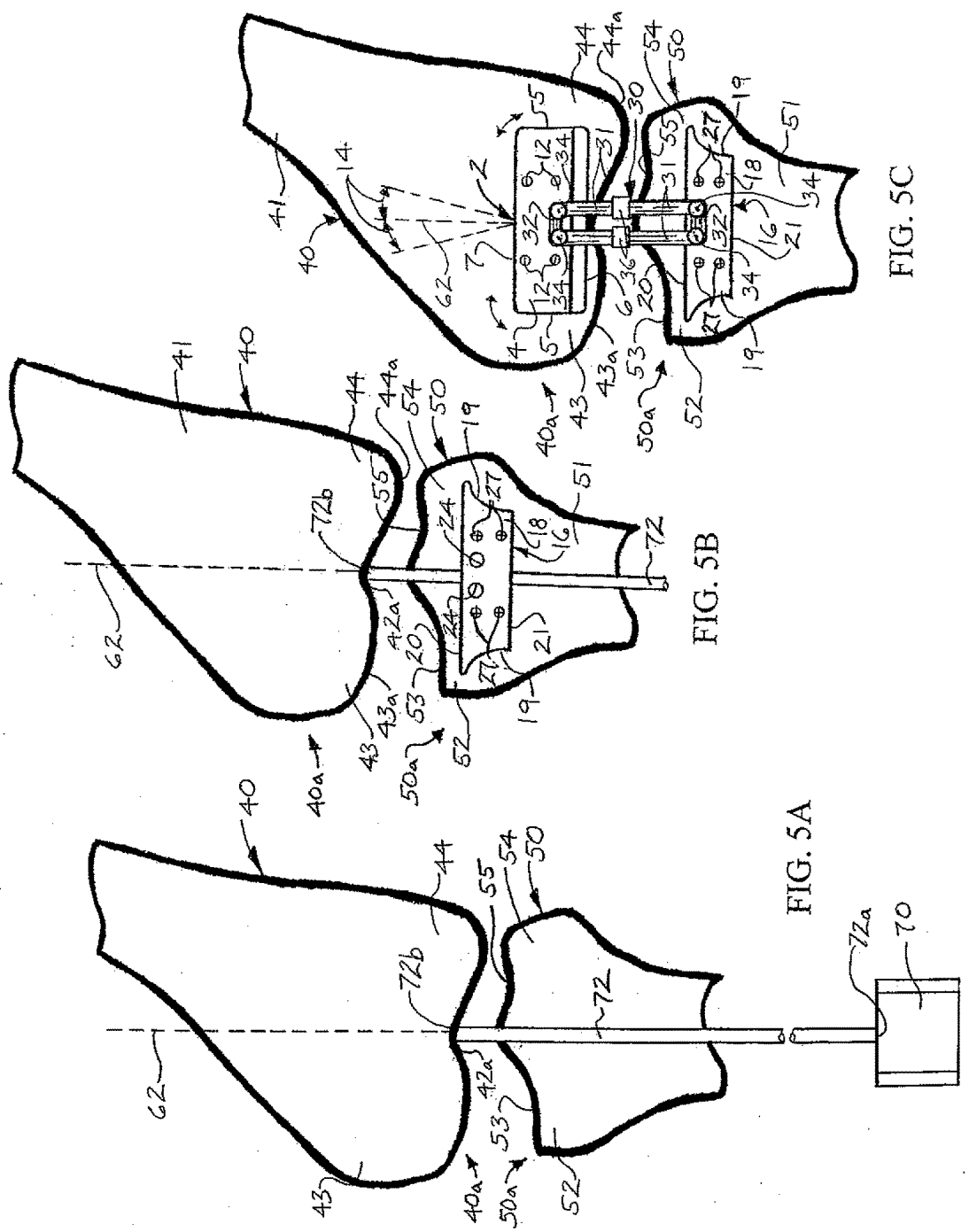

KNEE ARTHROPLASTY PREPARATION DEVICES AND METHODS

CROSS-REFERENCE TO RELATED APPLICATIONS

This application claims the benefit of U.S. provisional application no. 61/930,015, filed Jan. 22, 2014 and entitled KNEE ARTHROPLASTY PREPARATION DEVICES AND METHODS, which provisional application is incorporated by reference herein in its entirety.

FIELD

Illustrative embodiments of the disclosure generally relate to devices and methods used to prepare bone surfaces for prosthesis anchoring in knee arthroplasty procedures. More particularly, illustrative embodiments of the disclosure relate to minimally-invasive extra-medullary knee arthroplasty preparation devices and methods which enhance speed, accuracy and simplicity in performing total or partial arthroplasty procedures.

BACKGROUND

The background description provided herein is solely for the purpose of generally presenting the context of the illustrative embodiments of the disclosure. Aspects of the background description are neither expressly nor impliedly admitted as prior art against the claimed subject matter.

In partial and complete knee arthroplasty or replacement procedures, the articular surfaces of the femur and tibia may be prepared to accommodate and anchor the respective femoral and tibial prostheses of the replacement knee joint. The bone surface preparation may require that precise cuts, or osteotomies, be made to the femur and tibia to attain the correct angles for limb alignment and reduce the risk of early implant failure.

Various tools and methods have been described for preparation of bone surfaces to accommodate the femoral and tibial prosthesis components in arthroplasty procedures. The goal of the osteotomies is to precisely align the center of the femoral head, the center of the knee and the center of the ankle along a straight mechanical axis formed by the femur and tibia. Precision in performing the osteotomies and placing the prostheses may greatly influence the outcome of the procedure.

Conventional techniques for preparation of bone surfaces in arthroplasty procedures may include use of a guide system which guides the femoral and tibial osteotomies in separate procedures. According to the technique, a rod is inserted into a longitudinal cavity in the femur and the tibia. A femoral cutting block and a tibial cutting block are assembled on the rod in perpendicular orientation to the anatomical axis of the femur and the tibia, respectively. As the osteotomies are made, the cutting blocks guide a saw blade along a plane which is perpendicular to the anatomical axis of the femur and the tibia, respectively, to form the cuts which form extension gaps that will accommodate the femoral and tibial prostheses.

The conventional arthroplasty preparation techniques are associated with several drawbacks, including complications such as fat emboli. Moreover, the extension gaps are subject to error since these steps are performed separately from each other. Additionally, the centralizing femoral and tibial components' alignment with the anatomical axis is subject to error.

Accordingly, minimally-invasive, extra-medullary knee arthroplasty preparation devices and methods which increase the speed, accuracy and simplicity of performing total or partial arthroplasty are desirable.

SUMMARY

Illustrative embodiments of the disclosure are generally directed to knee arthroplasty preparation devices which increase the speed, accuracy and simplicity of performing total or partial arthroplasty. An illustrative embodiment of the knee arthroplasty preparation devices includes a tibial cutting block adapted for attachment to a tibia, a femoral cutting block adapted for attachment to a femur and a block positioning guide engaging the tibial cutting block and the femoral cutting block.

Illustrative embodiments of the disclosure are further generally directed to knee arthroplasty preparation methods. An illustrative embodiment of the knee arthroplasty preparation methods includes aligning a femur and a tibia in an extended position; aligning a longitudinal adjusting rod along a mechanical axis of the tibia; placing a tibial cutting block on the tibia and across the longitudinal adjusting rod, the tibial cutting block having a first cutting plane surface; aligning and adjusting the tibial cutting block using the longitudinal adjusting rod fastening the tibial cutting block to the tibia; placing a femoral cutting block on the femur, the femoral cutting block having a second cutting plane surface; aligning the femoral cutting block with the second cutting plane surface at an optimal angle to the first cutting plane surface of the tibial cutting block by adjusting the block positioning guide; fastening the femoral cutting block to the femur; cutting the tibia along the first cutting plane surface; and cutting the femur along the second cutting plane surface.

BRIEF DESCRIPTION OF THE DRAWINGS

Illustrative embodiments of the disclosure will now be described, by way of example, with reference to the accompanying drawings, in which:

FIG. 5A is an enlarged sectional view of the femur and tibia illustrating placement of a longitudinal adjusting rod and alignment of the femur and tibia along the mechanical axis using the longitudinal adjusting rod according to implementation off the illustrative knee arthroplasty method;

FIG. 5B is an enlarged sectional view of the femur and tibia with a tibial cutting block initially placed on the tibia and aligned with the mechanical axis via the longitudinal adjusting rod in implementation of the illustrative knee arthroplasty method;

FIG. 5C is an enlarged sectional view of the femur and tibia with the tibial cutting block secured to the tibia and a block positioning guide engaging and positioning the femoral cutting block relative to the tibial cutting block and the mechanical axis in implementation of the illustrative knee arthroplasty method;

DETAILED DESCRIPTION

The following detailed description is merely exemplary in nature and is not intended to limit the described embodiments or the application and uses of the described embodiments. As used herein, the word "exemplary" or "illustrative" means "serving as an example instance, or illustration." Any implementation described herein as "exemplary" of "illustrative" is not necessarily to be construed as preferred or advantageous over other implementations. All of the implementations described below are exemplary implementations provided to enable users skilled in the an to practice the disclosure and are not intended to limit the scope of the claims. Moreover, the illustrative embodiments described herein are not exhaustive and embodiments or implementations other than those which are described herein and which fall within the scope of the appended claims are possible. Furthermore, there is no intention to be bound by any expressed or implied theory presented in the preceding technical field, background, brief summary or the following detailed description.

Figure 3:
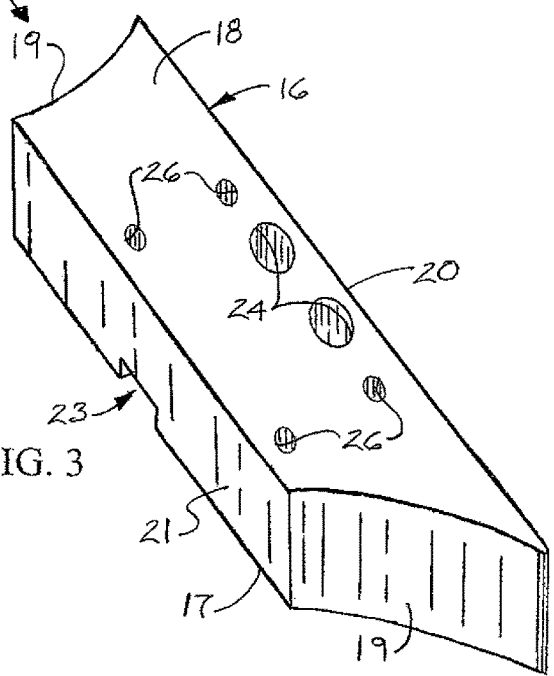
FIG. 3 is a perspective view of an exemplary tibial cutting block according to an illustrative embodiment of the knee anthroplasty devices.
Figure 4:
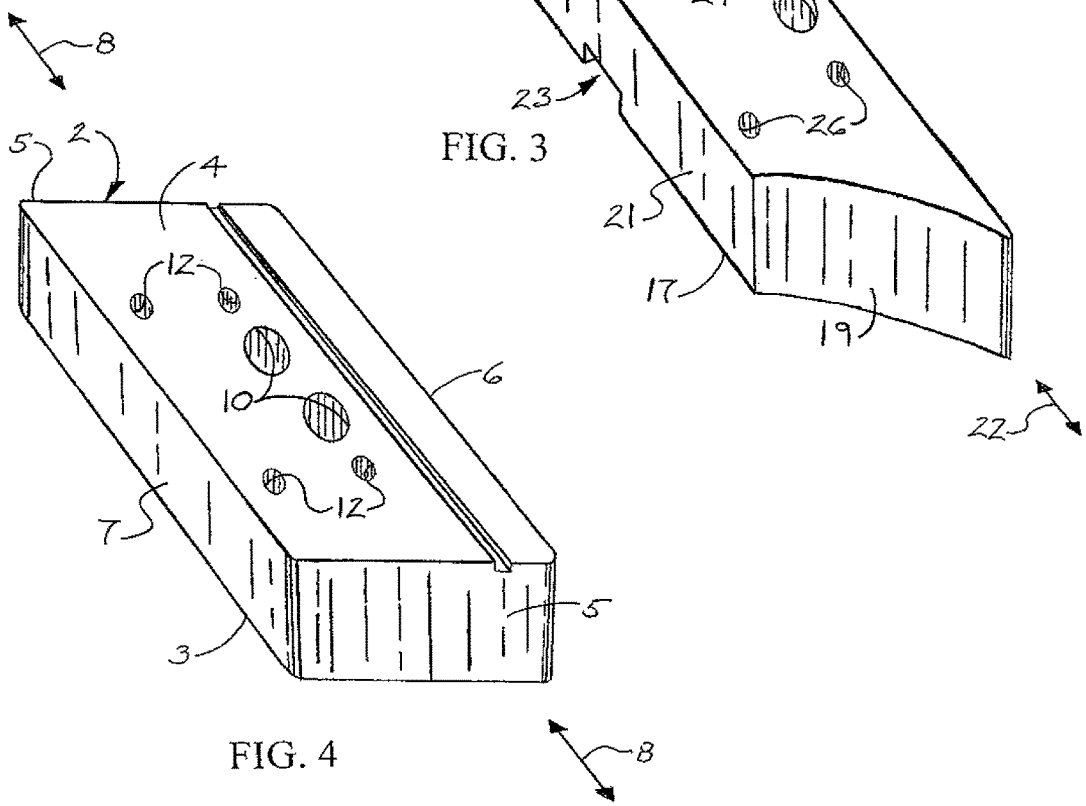
FIG. 4 is a perspective view of an exemplary femoral cutting block according illustrative embodiment of the knee arthroplasty devices.
Figure 5:
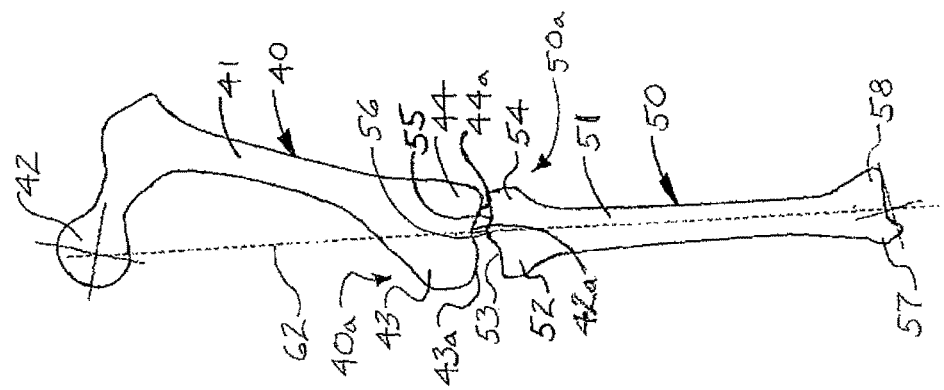
FIG. 5 is a front view of a femur and a tibia aligned along a mechanical axis preparatory to implementation of an illustrative embodiment of the knee arthroplasty methods.

Referring initially to FIGS. 1-5 of the drawings, an illustrative embodiment of the knee arthroplasty preparation devices, hereinafter device, is generally indicated by reference numeral 1. The device 1 includes a femoral cutting block 2 which, in a knee arthroplasty preparation method (hereinafter described), is positioned and fastened on the distal end 40a of a femur 40 of a knee arthroplasty patient and a tibial cutting block 16 which is positioned and fastened on the distal end 50a of a tibia 50 of the patient. A block positioning guide 30 connects the femoral cutting block 2 and the tibial cutting block 16 to facilitate alignment of the femoral cutting block 2 on the femur 40 relative to the tibial cutting block 16 on the tibia 50 for precise cutting of the femur 40 and the tibia 50, respectively, preparatory to the knee arthroplasty procedure. As illustrated in FIG. 5, the femur 40 of the patient includes a femoral shaft 41, a femoral head 42 at a proximal end of the femoral shaft 41 and a medial femoral condyle 43 and a lateral femoral condyle 44 at a distal end of the femoral shaft 41. The medial femoral condyle 43 and the lateral femoral condyle 44 have a medial condylar surface 43a and a lateral condylar surface 44a. respectively. A femoral trochlear groove 42a extends between the medial femoral condyle 43 and the lateral femoral condyle 44.

The tibia 50 of the patient includes a tibial shaft 51, a medial tibial condyle 52 and a lateral tibial condyle 54 at a proximal end and a medial malleolus 57 and a lateral malleolus 58 at a distal end of the tibial shaft 51. The medial tibial condyle 52 and the lateral tibial condyle 54 have a medial tibial plateau 53 and a lateral tibial plateau 55 which correspond positionally to the medial condylar surface 43a and the lateral condylar surface 44a, respectively, on the femur 40. An intercondylar eminence 56 protrudes between the medial tibial condyle 52 and the lateral tibial condyle 54. As further illustrated in FIG. 5, preparatory to carrying out the femoral and tibial osteotomies using the device 1, the femur 40 and the tibia 50 are oriented with a mechanical axis of the tibia 62 extending through the femoral head 42 and between the medial femoral condyle 43 and the lateral femoral condyle 44 of the femur 40. The mechanical axis 62 also extends through the intercondylar eminence 56 and between the medial malleolus 57 and the lateral malleolus 58 of the tibia 50. The mechanical axis 62 may also extend through the center of the ankle (not illustrated) of the patient.

As illustrated in FIG. 4, the femoral cutting block 2 of the device 1 may include a femoral contact surface 3, an outer femoral cutting block surface 4 which is opposite the femoral contact surface 3, a pair of side femoral cutting block surfaces 5, a femoral cutting block cutting plane surface 6 and a femoral cutting block proximal surface 7 which is opposite the femoral cutting block cutting plane surface 6. The femoral cutting block 2 may have a longitudinal femoral cutting block axis 8 which is parallel to the plane of the femoral cutting block cutting plane surface 6. A pair of spaced-apart block guide openings 10 may extend into the outer femoral cutting block surface 4 of the femoral cutting block 2. Multiple block fastener openings 12 may extend through the femoral cutting block 2 from the outer femoral cutting block surface 4 to the femoral contact surface 3. The femoral cutting block 2 may include metal, plastic, composite material and/or any other suitable material which is consistent with the functional requirements of the device 1.

As illustrated in FIG. 3, the tibial cutting block 16 of the device 1 may include a tibial contact surface 17, an outer tibial cutting block surface 18 which is opposite the tibial contact surface 17, a pair of side tibial cutting block surfaces 19, a tibial cutting block cutting plane surface 20 and a tibial cutting block distal surface 21 which is opposite the tibial cutting block cutting plane surface 20. The tibial cutting block 16 may have a longitudinal tibial cutting block axis 22 which is parallel to the plane of the cutting plane surface 20. A pair of spaced-apart block guide openings 24 may extend into the outer surface 18 of the tibial cutting block 16. Multiple block fastener openings 26 may extend through the tibial cutting block 16 from the outer tibial cutting block surface 18 to the tibial contact surface 17. A rod slot 23 may extend along the tibial contact surface 17 from the tibial cutting block cutting plane surface 20 to the tibial cutting block distal surface 21 of the tibial cutting block 16 for purposes which will be hereinafter described. The tibial cutting block 16 may include metal, plastic, composite material and/or any other suitable material which is consistent with the functional requirements of the device 1.

Figure 2:
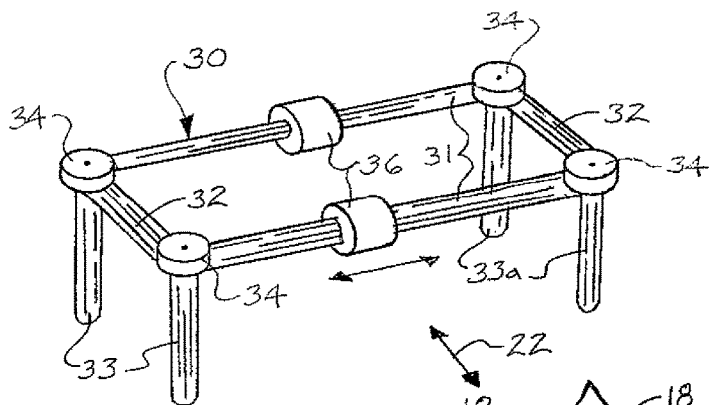
FIG. 2 is a perspective view of an exemplary block positioning guide according to an illustrative embodiment of the knee arthroplasty devices.

As illustrated in FIG. 2, the block positioning guide 30 of the device 1 may include a pair of generally elongated, parallel, spaced-apart longitudinal guide frames 31. A frame length adjusting mechanism 36 may be provided in each longitudinal guide frame 31 to render the block positioning guide 30 selectively longitudinally adjustable. The frame length adjusting mechanisms 36 may include threaded sleeves or any other suitable mechanisms which engage the longitudinal guide frames 31 to facilitate lengthwise adjustment of the longitudinal guide frames 31 and the block positioning guide 30. In some embodiments, the frame length adjusting mechanism 36 may be adapted for incremental longitudinal adjustment to selected lengths according to the knowledge of those skilled in the art. A pair of transverse guide frames 32 may conned the respective ends of the longitudinal guide frames 31 to each other. A pair of frame pivots 34 may pivotally attach the ends of each transverse guide frame 32 to the corresponding longitudinal guide frame 31. In some embodiments, the frame pivots 34 may be adapted for incremental angular adjustment to selected angles according to the knowledge of those skilled in the art. A first pair of spaced-apart block insertion rods 33 may extend from the respective ends of the transverse guide frame 32 at a first end of the block positioning guide 30. A second pair of spaced apart block insertion rods 33a may extend from the respective ends of the transverse guide frame 32 at a second end of the block positioning guide 30. The first pair of block insertion rods 33 of the block positioning guide 30 are sized and spaced for insertion into the respective block guide openings 10 (FIG. 4) in the femoral cutting block 2. Likewise, the second pair of block insertion rods 33a of the block positioning guide 30 are sized and spaced for insertion into the respective block guide openings 24 (FIG. 3) in the tibial cutting block 16.

Figure 1:
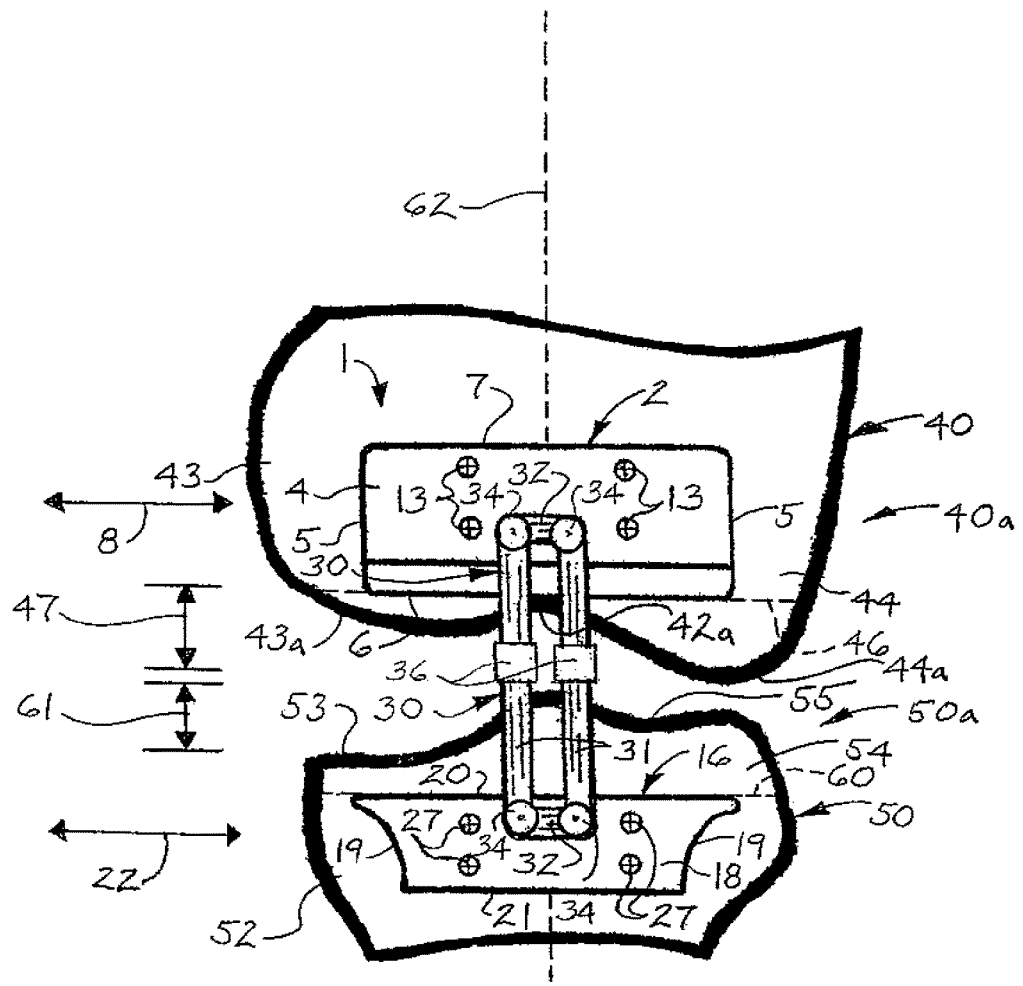
FIG. 1 is a top view of an illustrative embodiment of the knee arthroplasty devices in exemplary implementation thereof.
Figure 7:
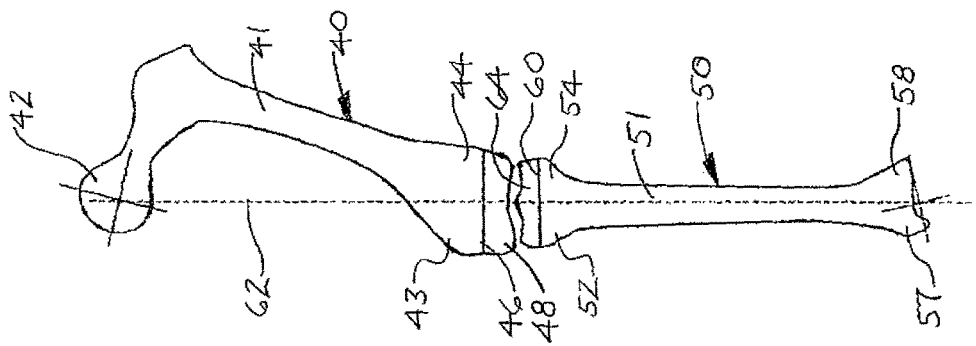
FIG. 7 is a front view of the femur and tibia after installation of a femoral prosthesis and a tibial prosthesis.

As further illustrated in FIG. 1 and will be hereinafter described, after alignment of the femoral cutting block 2 on the femur 40 and the tibial cutting block 16 on the tibia 50 using the block positioning guide 30, block fasteners 13 may be extended through the respective block fastener openings 12 in the femoral cutting block 2 and threaded into respective fastener openings 45 (FIG. 5F) in the underlying femur 40 to fasten the femoral cutting block 2 to the femur 40. Likewise, block fasteners 27 may be extended through the respective block fastener openings 26 in the tibial cutting block 16 and threaded into respective fastener openings 59 (FIG. 5F) in the underlying tibia 50 to fasten the tibial cutting block 16 to the tibia 50. Accordingly, as illustrated in FIG. 1, the femoral cutting block cutting plane surface 6 of the femoral cutting block 2 forms a femoral cutting plane 46 along which the femur 40 is cut to prepare the femur 40 for attachment of a femoral prosthesis 48 (FIG. 7). Likewise, the femoral cutting block cutting plane surface 20 of the tibial cutting block 16 forms a tibial cutting plane 60 along which the tibia 50 is cut to prepare the tibia 50 for attachment of a tibial prosthesis 64 (FIG. 7) as will be hereinafter further described.

Figure 6:
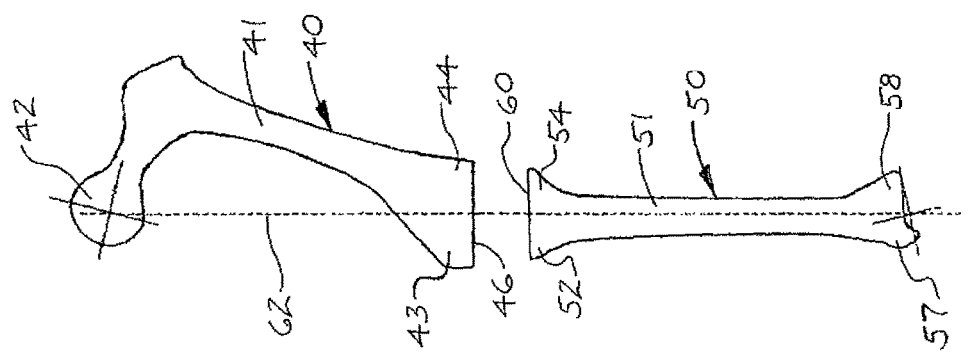
FIG. 6 is a front view of the femur and tibia after completion of the femoral and tibial osteotomies according to an illustrative embodiment of the knee arthroplasty methods.

Referring next to FIGS. 5-7 of the drawings, exemplary application of the device 1 according to an illustrative embodiment of the knee arthroplasty preparation methods is illustrated. The distal end 40a of the femur 40 and the proximal end 50a of the tibia 50 are initially surgically exposed and the femur 40 and the tibia 50 are aligned in an extended position using a standard surgical approach and tissue preparation such as in the conventional manner. As illustrated in FIG. 5, the femur 40 and the tibia 50 of the patient are aligned such that the mechanical axis of the tibia 62 extends through the femoral head 42 and between the medial femoral condyle 43 and the lateral femoral condyle 44 of the femur 40 and through the intercondylar eminence 56 and between the medial malleolus 57 and the lateral malleolus 58 of the tibia 50. As illustrated in FIG. 5A, to this end, an ankle clamp 70 may be installed on the ankle (not illustrated) of the patient. A longitudinal adjusting rod 72 has a distal rod end 72a which may be placed at the ankle clamp 70 and a proximal rod end 72b which may be placed at the femoral trochlear groove 42a of the femur 40. Accordingly, the longitudinal adjusting rod 72 extends along and parallel to the mechanical axis 62. The longitudinal adjusting rod 72 may be fastened or pinned in place. The ankle clamp 70 may have any design or component features such as straps, for example and without limitation, which facilitate fastening of the ankle clamp 70 to the ankle of the patient.

As illustrated in FIG. 5B, the tibial cutting block 16 may next be placed on the distal end 50a of the tibia 50 and across the longitudinal adjusting rod 72 with the longitudinal adjusting rod 72 extending through the rod slot 23 (FIG. 3). Accordingly, the longitudinal adjusting rod 72 maintains the cutting plane surface 20 on the tibial cutting block 16 in perpendicular relationship to the mechanical axis 62. The position of the tibial cutting block 16 along the longitudinal adjusting rod 72 and with respect to the distal end 50a of the tibia 50 may be aligned and adjusted to select the position of the tibial cutting plane 60 (FIG. 1) using the longitudinal adjusting rod 72 and the joint line surface, respectively. The thickness of bone material which remains beyond the tibial cutting plane 60 and which will be removed from the tibia 50, as will be hereinafter described, defines a tibial extension gap 61 corresponding to the thickness of the tibial prosthesis 64 (FIG. 7) which will be installed on the tibia 50. Fastener openings 59 (FIG. 5F) may be drilled through the block fastener openings 26 in the tibial cutting block 16 and into the underlying tibia 50. Block fasteners 27 may be extended through the block fastener openings 26 and threaded into the underlying fastener openings 59 to secure the tibial cutting block 16 in place on the tibia 50.

Figures 5D, 5E, 5F:
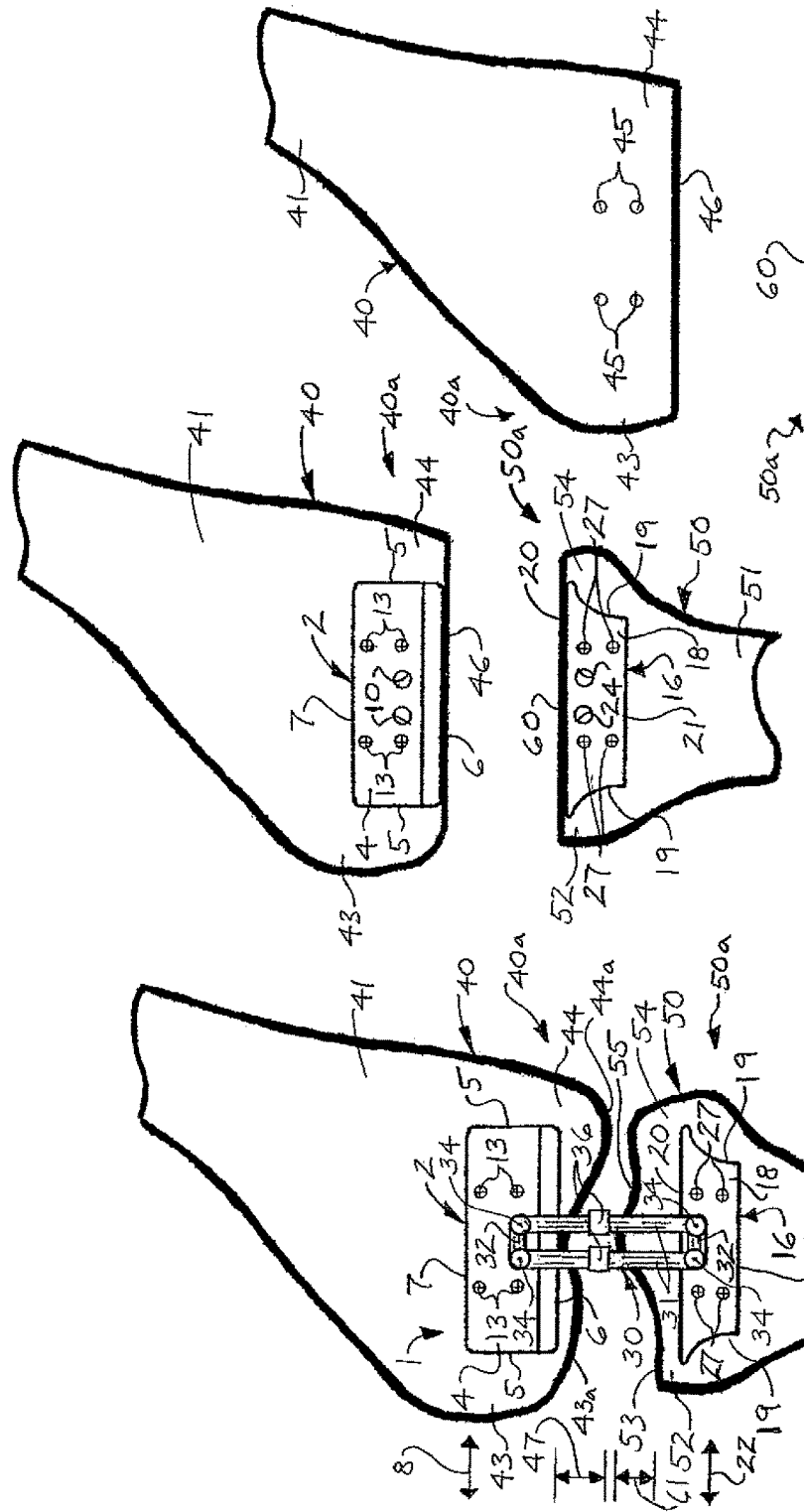
FIG. 5D is an enlarged sectional view of the femur and tibia with block listeners securing the femoral cutting block and the tibial cutting block on the femur and tibia, respectively, as the block positioning guide remains in place.
FIG. 5E is an enlarged sectional view of the femur and tibia with the block positioning guide removed from the cutting blocks and the block fasteners still securing the femoral cutting block and the tibial cutting block on the femur and tibia, respectively, preparatory to osteotomies carried out on the femur and tibia.
FIG. 5F is an enlarged sectional view of the femur and tibia with the femoral cutting block and the tibial cutting block removed from the femur and tibia, respectively, after the osteotomies.

As illustrated in FIG. 5C, the femoral cutting block 2 may next be placed on the distal end 40a of the femur 40. The block positioning guide 30 may be used to connect the femoral cutting block 2 to the tibial cutting block 16 by insertion of the first pair of block insertion rods 33 (FIG. 2) into the respective block guide openings 24 in the tibial cutting block 16 and insertion of the second pair of block insertion rods 33a (FIG. 2) into the respective block guide openings 10 in the femoral cutting block 2. Accordingly, the block positioning guide 30 precisely aligns the cutting plane surface 6 on the femoral cutting block 2 into parallel relationship with the cutting plane surface 20 on the tibial cutting block 16. The position of the femoral cutting block 2 with respect to the distal end 40a of the femur 40 may be adjusted to select the position of the femoral cutting plane 46 (FIG. 1) by selectively lengthening or shortening the block positioning guide 30 using the frame length adjusting mechanisms 36. The valgus angle 14 (FIG. 5C) of the femoral cutting block 2 relative to the mechanical axis 62 can be selectively adjusted by pivoting the longitudinal guide frames 31 relative to the transverse guide frames 32 at the frame pivots 34. The valgus angle 14 may be determined pre-operatively using conventional techniques. The thickness of bone material which remains beyond the femoral cutting plane 46 and which will be removed from the femur 40, as will be hereinafter described, defines a femoral extension gap 47 (FIG. 5D) corresponding to the thickness of the femoral prosthesis 48 (FIG. 7) which will be installed on the femur 40. The block positioning guide 30 may be used to adjust the femoral extension gap 47 and guide the femoral cutting block 2 at an optimal angle (typically about 0-10 degrees) to the cutting plane surface 20 on the tibial cutting block 16. Fastener openings 45 (FIG. 5F) may be drilled through the block fastener openings 12 (FIG. 4) in the femoral cutting block 2 into the underlying femur 40. As illustrated in FIG. 5D, block fasteners 13 may be extended through the block fastener openings 12 and threaded into the underlying fastener openings 45 to secure the femoral cutting block 2 in place on the femur 40.

As illustrated in FIG. 5F, the block positioning guide 30 may next be removed from the block guide openings 24 in the tibial cutting block 16 and the block guide openings 10 in the femoral cutting block 2. As illustrated in FIGS. 5E and 6, the tibial cutting plane 60 may be cut in the distal end 50a of the tibia 50 with the cutting plane surface 20 serving as a guide or template for the tibial cutting plane 60. In like manner, a femoral cutting plane 46 may be cut in the distal end 40a of the femur 40 with the cutting plane surface 6 of the femoral cutting block 2 serving as a guide or template for the femoral cutting plane 46. As illustrated in FIGS. 1 and 5D, the thickness of bone material which is cut from the tibia 50 corresponds to a tibial extension gap 61 which equals the thickness of the tibial prosthesis 64 (FIG. 7) that will be installed at the tibial cutting plane 60 of the tibia 50. Likewise, the thickness of bone material which is cut from the femur 40 corresponds to a femoral extension gap 47 which equals the thickness of the femoral prosthesis 48 (FIG. 7) that will be installed at the femoral cutting plane 46 of the femur 40.

As illustrated in FIG. 5F, the tibial cutting block 16 (FIG. 5E) may and be removed from the tibia 50 after removal of the block fasteners 27 from the block fastener openings 26. In like manner, the femoral cutting block 2 may be removed from the femur 40 after removal of the block fasteners 13 from the block fastener openings 12. As illustrated in FIG. 7, after additional preparation of the bone surfaces at the tibial cutting plane 60 and the femoral cutting plane 46, the tibial prosthesis 64 is installed on the tibia 50 and the femoral prosthesis 48 is installed on the femur 40, typically in the conventional manner, after which the surgical procedure is completed.

Figure 8A:
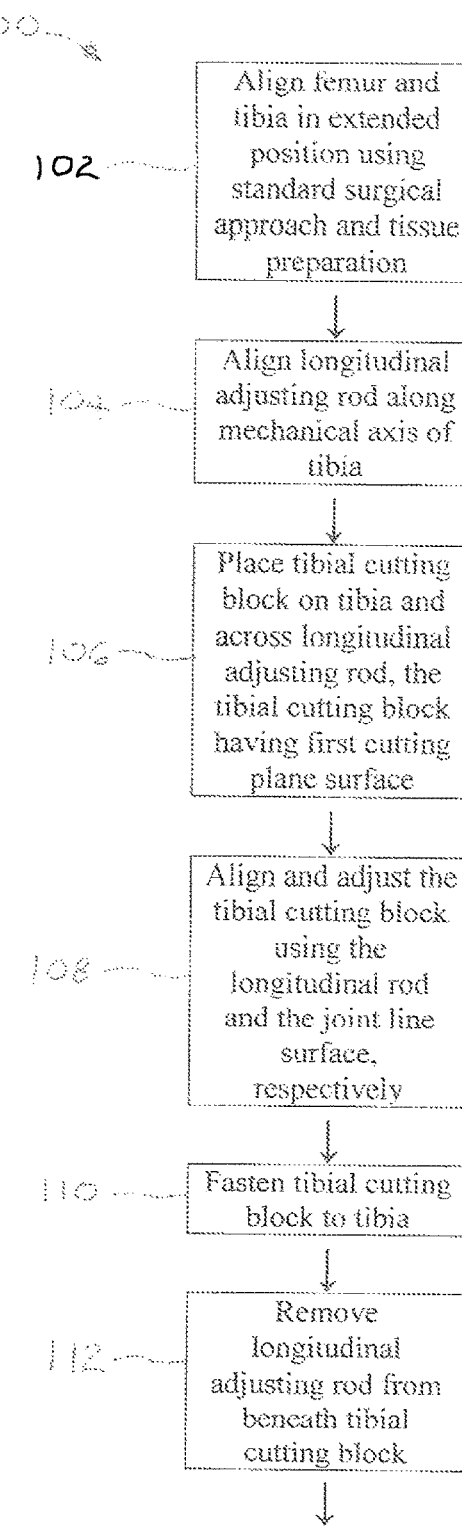
FIG. 8A is a flow diagram of an illustrative embodiment of the knee arthroplasty preparation methods.
Figure 8B:
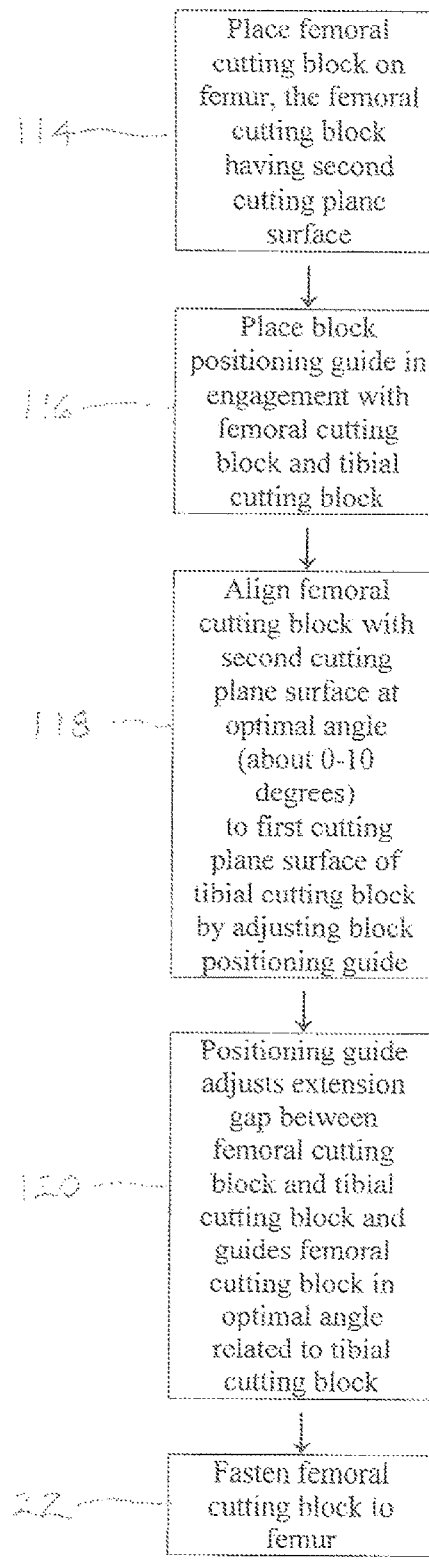
FIG. 8B is a flow diagram which is a continuation of the illustrative knee arthroplasty preparation method illustrated in FIG. 8A.
Figure 8C:
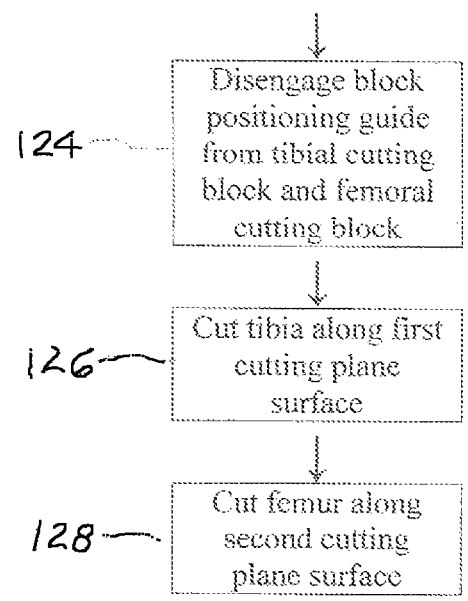
FIG. 8C is a flow diagram which is a continuation of the illustrative knee arthroplasty preparation method illustrated in FIG. 8B.

Referring next to FIGS. 8A-8C of the drawings, a flow diagram 100 of an illustrative embodiment of the knee arthroplasty preparation methods is illustrated. At block 102, a femur and a tibia of a patient are aligned in an extended position using a standard surgical approach and tissue preparation. At block 104, a longitudinal adjusting rod is aligned along a mechanical axis of the tibia. At block 106, a tibial cutting block having a first cutting plane surface is placed on the tibia und across the longitudinal adjusting rod. At block 108, the tibial cutting block is aligned and adjusted using the longitudinal adjusting rod and the joint line surface, respectively. At block 110, the tibial cutting block is fastened to the tibia. At block 112, the longitudinal adjusting rod may be removed from beneath the tibial cutting block. At block 114, a femoral cutting block having a second cutting plane surface is placed on the femur. At block 116, a block positioning guide is placed in engagement with the femoral cutting block and the tibial cutting block. At block 118, the femoral cutting block is aligned with the second cutting plane surface of the femoral cutting block at an optimal angle (typically about 0-10 degrees) to the first cutting plane surface of the tibial cutting block by adjusting the block positioning guide. At block 120, the positioning guide may be used to adjust an extension gap between the femoral cutting block and the tibial cutting block and guide the femoral cutting block at the optimal angle related to the tibal cutting block. At block 122, the femoral cutting block is fastened to the femur. At block 124, the block positioning guide is disengaged from the tibial cutting block and the femoral cutting block. At block 126, the tibia is cut along the first cutting plane surface of the tibial cutting block. At block 128, the femur is cut along the second cutting plane surface of the femoral cutting block.

While certain illustrative embodiments of the disclosure have been described above, it will be recognized and understood that various modifications can be made to the embodiments and the appended claims are intended to cover all such modifications which may fall within the spirit and scope of the disclosure.

What is claimed is:

1. An extramedullary knee arthroplasty preparation device for precise cutting of a femur and a tibia preparatory to a knee arthroplasty procedure, comprising:
    a longitudinal adjusting rod for extension along and parallel to a mechanical axis of the tibia;
    a tibial cutting block adapted for attachment to a tibia, the tibial cutting block positional across the longitudinal adjusting rod;
    a femoral cutting block adapted for attachment to a femur;
    a block positioning guide configured to engage the tibial cutting block and the femoral cutting block, the block positioning guide including a pair of elongated, parallel, spaced-apart longitudinal guide frames and a pair of transverse guide frames connecting the longitudinal guide frames and the pair of longitudinal guide frames pivotal with respect to the pair of transverse guide frames; and
    a valgus angle of the femoral cutting block relative to the mechanical axis is selectively adjustable by pivoting the longitudinal guide frames relative to the transverse guide frames of the block positioning guide.

2. The extramedullary knee arthroplasty preparation device of claim 1 wherein the tibial cutting block comprises a first pair of block guide openings and the femoral cutting block comprises a second pair of block guide openings, and the block positioning guide engages the first pair of block guide openings and the second pair of block guide openings.

3. The extramedullary knee arthroplasty preparation device of claim 1 further comprising a plurality of block fastener openings extending through each of the tibial cutting block and the femoral cutting block.

4. The extramedullary knee arthroplasty preparation device of claim 1 wherein a first pair of block insertion rods and a second pair of block insertion rods carried by the transverse guide frames, respectively, the first pair of block insertion rods and the second pair of block insertion rods engaging the tibial cutting block and the femoral cutting block, respectively.

5. The extramedullary knee arthroplasty preparation device of claim 4 wherein the tibial cutting block comprises a first pair of block guide openings and the femoral cutting block comprises a second pair of block guide openings, and the first pair of block insertion rods of the block positioning guide is inserted in the first pair of block guide openings, respectively, and the second pair of block insertion rods of the block positioning guide is inserted in the second pair of block guide openings, respectively.

6. The extramedullary knee arthroplasty preparation device of claim 4 wherein each of the longitudinal guide frames is selectively length-adjustable.

7. The extramedullary knee arthroplasty preparation device of claim 1 further comprising a rod slot in the tibial cutting block.

8. The extramedullary knee arthroplasty preparation device of claim 1 wherein the tibial cutting block comprises a tibial contact surface, an outer tibial cutting block surface opposite the tibial contact surface, a pair of side tibial cutting block surfaces extending between the tibial contact surface and the outer tibial cutting block surface, and a tibial cutting block cutting plane surface and a tibial cutting block distal surface extending between the pair of side tibial cutting block surfaces.

9. The extramedullary knee arthroplasty preparation device of claim 1 wherein the femoral cutting block comprises a femoral contact surface, an outer femoral cutting block surface opposite the femoral contact surface, a pair of side femoral cutting block surfaces extending between the femoral contact surface and the outer femoral cutting block surface, and a femoral cutting block cutting plane surface and a femoral cutting block proximal surface extending between the pair of side femoral cutting block surfaces.

10. A knee arthroplasty preparation method, comprising:
providing an extramedullary knee arthroplasty preparation device including:
a longitudinal adjusting rod for extension along and parallel to a mechanical axis of the tibia;
a tibial cutting block adapted for attachment to a tibia, the tibial cutting block positional across the longitudinal adjusting rod;
a femoral cutting block adapted for attachment to a femur;
a block positioning guide configured to engage the tibial cutting block and the femoral cutting block, the block positioning guide including a pair of elongated, parallel, spaced-apart longitudinal guide frames and a pair of transverse guide frames connecting the longitudinal guide frames and the pair of longitudinal guide frames pivotal with respect to the pair of transverse guide frames; and
a valgus angle of the femoral cutting block relative to the mechanical axis is selectively adjustable by pivoting the longitudinal guide frames relative to the transverse guide frames of the block positioning guide;
aligning a femur and a tibia in an extended position;
placing the tibial cutting block on the tibia, the tibial cutting block having a first cutting plane surface;
aligning and adjusting the tibial cutting block;
fastening the tibial cutting block to the tibia;
placing the femoral cutting block on the femur, the femoral cutting block having a second cutting plane surface;
placing the block positioning guide in engagement with the femoral cutting block and the tibial cutting block;
aligning the femoral cutting block with the second cutting plane surface at an optimal angle to the first cutting plane surface of the tibial cutting block by adjusting the block positioning guide;
fastening the femoral cutting block to the femur;
cutting the tibia along the first cutting plane surface; and
cutting the femur along the second cutting plane surface.

11. The knee arthroplasty preparation method of claim 10 wherein aligning and adjusting the tibial cutting block comprises aligning the longitudinal adjusting rod along the mechanical axis of the tibia and orienting the first cutting plane surface perpendicular to the longitudinal adjusting rod.

12. The knee arthroplasty preparation method of claim 10 wherein placing the block positioning guide in engagement with the femoral cutting block and the tibial cutting block comprises providing the block positioning guide including a first pair of block insertion rods and a second pair of block insertion rods carried by the transverse guide frames, respectively, and inserting the first pair of block insertion rods in a first pair of block guide openings in the tibial cutting block and inserting the second pair of block insertion rods in a second pair of block guide openings in the femoral cutting block.

13. The knee arthroplasty preparation method of claim 12 further comprising adjusting the femoral cutting block on the femur by longitudinally adjusting the longitudinal guide frames of the block positioning guide.

14. A knee arthroplasty preparation method, comprising:
providing an extramedullary knee arthroplasty preparation device including:
a longitudinal adjusting rod for extension along and parallel to a mechanical axis of the tibia;
a tibial cutting block adapted for attachment to a tibia, the tibial cutting block positional across the longitudinal adjusting rod;
a femoral cutting block adapted for attachment to a femur;
a block positioning guide configured to engage the tibial cutting block and the femoral cutting block, the block positioning guide including a pair of elongated, parallel, spaced-apart longitudinal guide frames and a pair of transverse guide frames connecting the longitudinal guide frames and the pair of longitudinal guide frames pivotal with respect to the pair of transverse guide frames; and
a valgus angle of the femoral cutting block relative to the mechanical axis is selectively adjustable by pivoting the longitudinal guide frames relative to the transverse guide frames of the block positioning guide;
aligning a femur and a tibia in an extended position;
aligning the longitudinal adjusting rod along the mechanical axis of the tibia;
placing the tibial cutting block on the tibia and across the longitudinal adjusting rod, the tibial cutting block having a first cutting plane surface;
aligning and adjusting the tibial cutting block using the longitudinal adjusting rod;
fastening the tibial cutting block to the tibia;
removing the longitudinal adjusting rod from beneath the tibial cutting block;
placing the femoral cutting block on the femur, the femoral cutting block having a second cutting plane surface;
placing the block positioning guide in engagement with the femoral cutting block and the tibial cutting block;
aligning the femoral cutting block with the second cutting plane surface at an optimal angle to the first cutting plane surface of the tibial cutting block by adjusting the block positioning guide;
fastening the femoral cutting block to the femur;
disengaging the block positioning guide from the tibial cutting block and the femoral cutting block;
cutting the tibia along the first cutting plane surface; and
cutting the femur along the second cutting plane surface.

15. The knee arthroplasty preparation method of claim 14 wherein aligning and adjusting the tibial cutting block using the longitudinal adjusting rod comprises aligning the longitudinal adjusting rod along the mechanical axis of the tibia and orienting the first cutting plane surface perpendicular to the longitudinal adjusting rod.

16. The knee arthroplasty preparation method of claim 14 wherein placing the block positioning guide in engagement with the femoral cutting block and the tibial cutting block comprises providing the block positioning guide including a first pair of block insertion rods and a second pair of block insertion rods carried by the transverse guide frames, respectively, and inserting the first pair of block insertion rods in a first pair of block guide openings in the tibial cutting block and inserting the second pair of block insertion rods in a second pair of block guide openings in the femoral cutting block.

17. The knee arthroplasty preparation method of claim 16 further comprising adjusting the femoral cutting block on the femur by longitudinally adjusting the longitudinal guide frames of the block positioning guide.

\* \* \* \* \*